United States Patent [19]

Nesmeyanov et al.

[11] 3,957,841
[45] May 18, 1976

[54] PROCESS FOR PREPARING THE SODIUM SALT OF o-CARBOXYBENZOYL FERROCENE

[76] Inventors: Alexandr Nikolaevich Nesmeyanov, Glavnoe zdanie MGU, korpus "K", kv. 105, Moscow; Ljubov Grigorievna Bogomolova, ulitsa Nekrasova, 60, kv. 131, Leningrad; Nadezhda Sergeevna Kochetkova, ulitsa Garibaldi, 23/56, korpus 4, kv. 27, Moscow; Vera Dmitrievna Vilchevskaya, ulitsa Dmitria Ulyanova, 4, korpus 2, kv. 47, Moscow; Nikanor Petrovich Palitsyn, ulitsa Stankevicha, 12, kv. 10, Moscow; Julia Julievna Gorelikova, Nagatinskaya ulitsa, 58, korpus 2, kv. 73, Moscow; Irina Gennadievna Andrianova, prospket Smirnova, 43, kv. 27, Leningrad; Olga Petrovna Belozerova, prospekt Mira, 124, korpus 15, kv. 72; Vera Khusainovna Sjundjukova, ulitsa Vavilova, 44/2, kv. 154, both of Moscow, all of U.S.S.R.

[22] Filed: Aug. 14, 1974

[21] Appl. No.: 497,501

Related U.S. Application Data

[60] Division of Ser. No. 423,533, Dec. 10, 1973, abandoned, which is a continuation of Ser. No. 119,356, Feb. 26, 1971, abandoned.

[52] U.S. Cl.................... 260/439 CY; 260/429 CY
[51] Int. Cl.$^2$......................................... C07F 15/02
[58] Field of Search .............................. 260/439 CY

[56] References Cited
UNITED STATES PATENTS 3,035,978   5/1962   Jones et al. ................... 260/439 CY
3,078,291   2/1963   Stephenson ................... 260/439 CY
3,099,669   7/1963   Leigh ............................ 260/439 CY

OTHER PUBLICATIONS

Derwent Publication Abstracting USSR 179309 Publ. Aug. 1966; Chem. Abstracts, V65, 2300 (1966).

Chem. Abstracts, V55, 21080c (1961).

Chem. Abstracts, V58, 9133e (1964).

Merck Manual, 1972, 12th Edition pp. 255–257, 952, 969–972.

Goodman et al. The Pharmacological Basis of Therapeutics, 3rd Edition, 1965 pp. 1403–1406.

Stedman's Medical Dictionary (1966) pp. 1158, 1181, 1205.

*Primary Examiner*—Helen M. S. Sneed
*Attorney, Agent, or Firm*—Haseltine, Lake & Waters

[57] ABSTRACT

This invention relates to a novel medicinal preparation for treating maladies caused by iron deficiency comprising the sodium salt of o-carboxybenzoylferrocene as the active component.

The process for preparing the sodium salt of o-carboxybenzoylferrocene consists in that reacting phthalic anhydride with ethyl alcohol at the alcohol boiling temperature, whereupon the monoethyl o-phthalate obtained is treated with thionyl chloride, after which the obtained monoethyl o-phthalate chloride is used for acylating ferrocene in the presence of a catalyst in methylene chloride medium with heating, with subsequent saponification of the obtained o-carboxylbenzoylferrocene ester and separation of the end product.

3 Claims, No Drawings

PROCESS FOR PREPARING THE SODIUM SALT OF O-CARBOXYBENZOYL FERROCENE

This application is a Divisional Application of Ser. No. 423,533, filed Dec. 10, 1973, which was a continuation application of Ser. No. 119,356, filed Feb. 26, 1971, both now abandoned.

The present invention relates to a novel medicinal preparation for treating maladies caused by iron deficiency in the human organism, and to a process for preparing the active component of said medicinal preparation.

According to the invention, the medicinal preparation for treating maladies caused by iron deficiency comprises as its active component the sodium salt of o-carboxybenzoyl ferrocene of the following formula

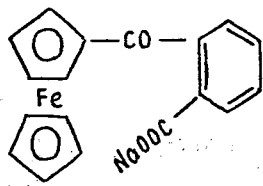

Said preparation has a strong stimulating effect upon the processes of blood formation. The preparation is readily soluble in water and is non-toxic. When introduced internally, it decomposes to yield active iron which is absorbed rapidly from the gastrointestinal tract. Most of the iron absorbed is used to build new molecules of hemoglobin, as well as of hemo-containing enzymes (catalase, pyroxidase, etc.), while the rest is deposited in the liver and spleen to replenish the iron depot in the organism.

The medicinal preparation of the invention may be used for treating hypochromic iron-deficiency anemia of diverse nature (posthemorrhagic, gastrogenic, agastric, anenteral, chlorosis, infantile anemia, etc.).

The preparation has been tested in clinics on more than 500 anemia patients. The preparation (sodium salt of o-carboxybenzoyl ferrocene) was prescribed internally, 0.3 g three times a day. The treatment lasted from 20 to 30 days.

The use of the preparation by anemia patients caused general improvement, reduced weakness, vertigo and palpitation, normalized integuments, reduced nail fragility.

When investigating peripheral blood, a rapid increase of hemoglobin content was observed, as well as of the number of erythrocytes, the color index rose markedly.

As shown by the clinical investigations of the preparation, on the fifth-eighth day reticulocyte crisis was observed. An average reticulocyte content was 90 per milles %. In the case of some patients the number of reticulocytes reached 165 per milles %. An average hemoglobin growth was 1.5 to 2 units a day.

In the case of almost all of the patients the serum iron content reached the norm or increased. Simultaneously, there was observed an increase in the number of erythrocytes from 220 thousand to 1,100 thousand. A number of patients showed an increase of leucocytes and thrombocytes.

The preparation of the invention is effective in treating hypochromic anemia in cases when other anti-anemia remedies are ineffective (reduced iron, ferric lactate, etc.).

The preparation is used in the pure state or in combination with a known pharmaceutical filler for tablets.

The medicinal preparation is used in the form of tablets of 0.34 g containing the active principle in the amount of 0.3 g and iron in the amount of 0.04g. When pure (i.e., sodium salt of o-carboxybenzoyl ferrocene), the preparation is a bitter dark-orange powder.

The preparation is stable and has no side effects. In some cases the preparation can cause a nauseous sensation during the first days of treatment, however, this cannot serve a sufficient ground for not using the preparation. The preparation has no contraindications for use. In the course of treatment the patients urine is colored red due to partial removal of the preparation by way of the kidneys.

This invention also relates to a novel process for preparing the sodium salt of o-carboxybenzoyl ferrocene, the active principle of the proposed medicinal preparation.

A process for preparing the sodium salt of o-carboxybenzoyl ferrocene is known according to which phthalic anhydride is reacted with methyl alcohol. The resulting product is monomethyl o-phthalate (o-carbomethoxybenzoic acid).

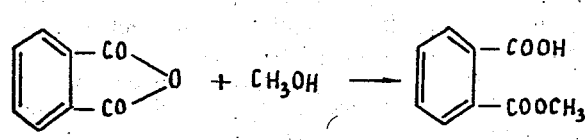

The resulting ester is crystallized, then ground and mixed with small batches of an agent substituting the hydroxy group with chlorine, with stirring at a temperature of 35°C. The resulting monomethyl o-phthalate chloride is reacted with ferrocene in carbon disulfide in the presence of aluminum chloride as a catalyst, in the form of a suspension in absolute ether.

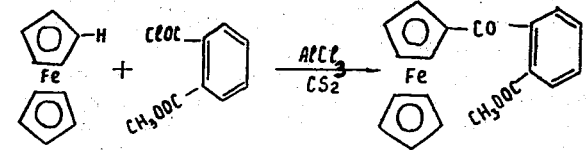

Subsequent saponification of o-carbomethoxybenzoyl ferrocene yields the sodium salt of o-carboxybenzoyl ferrocene

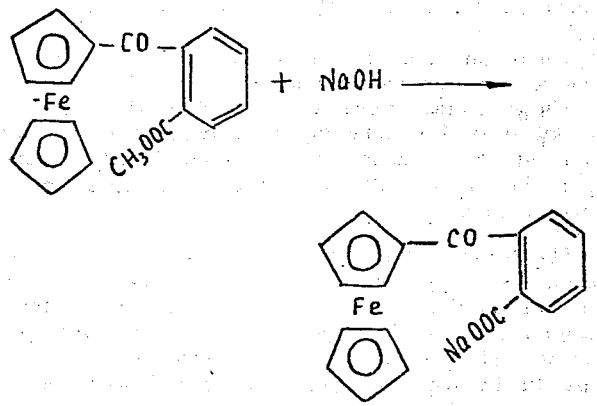

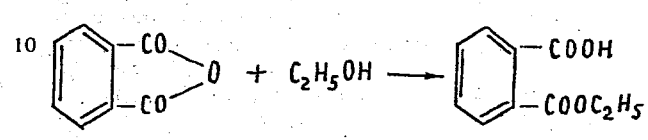

(cf., Doklady Akademii Nauk SSSR /Proceeding of the USSR Academy of Sciences/, vol. 118, No.3,513 (1958); USSR Inventor's Certificate No. 179,309).

According to the known process, at the first stage of the synthesis of monomethyl o-phthalate methyl alcohol is reacted with phthalic anhydride to yield a solid product after the distillation of the solvent. In order to use the product, it should at the next stage be dried, ground and once again charged in to the apparatus. This brings about a technological complication in the process, increased losses and reduced yield of the end product. Moreover, the use as catalyst of aluminum chloride in the form of a suspension in absolute ether during ferrocene acylation presents difficulties in operation under factory conditions.

Also a disadvantage of the known process is the use of toxic methyl alcohol and carbon disulfide, which calls for additional purification of the end product when using it for medicinal purposes.

The principal object of the present invention is to obtain a high-quality end product suitable for medicinal purposes.

Another object of the invention is to simplify the technology of the process.

Said principal and other objects of the present invention have been attained in a process for preparing the sodium salt of o-carboxybenzoyl ferrocene, the active principle of the proposed medicinal preparation, by reacting phthalic anhydride with a lower aliphatic alcohol while heating, treating the obtained monophthalate with an agent substituting the hydroxy group with chlorine, acylating ferrocene with the obtained alkyl o-phthalate chloride in the presence of a catalyst in an organic solvent medium while heating and with subsequent saponification of the obtained o-carboxybenzoyl ferrocene ester and separation of the end product, in which process, according to the invention, ethyl alcohol is used as the lower aliphatic alcohol, thionyl chloride is used as the agent substituting the hydroxy group with chlorine, and the process of acylating ferrocene with ethyl o-phthalate chloride is carried out in a methylene chlorine medium.

With the object of increasing the yield and improving the quality of the end product, used as the catalyst is a suspension of aluminum chloride in methylene chloride or a suspension of aluminum chloride in higher ether.

The process according to the present invention is effected in the following manner.

In an apparatus equipped with a heating jacket, reflux condenser and a stirrer are placed phthalic anhydride and absolute ethyl alcohol which are heated with stirring at the alcohol boiling temperature to complete dissolution of the phthalic anhydride. Then, heating is continued for 30 minutes more and the excess alcohol is distilled under vacuum at a temperature not exceeding 50°C.

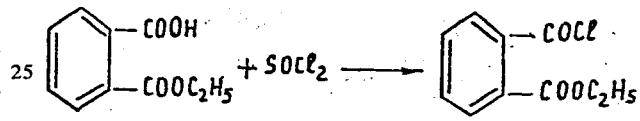

Thionyl chloride cooled to 20°C is added in small increments to the residue from the vacuum distillation.

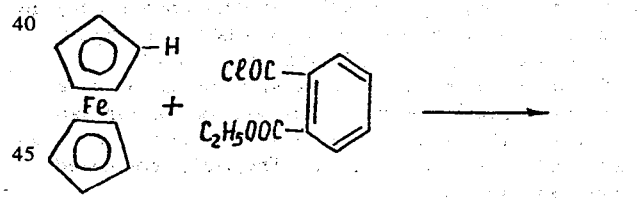

The reaction mixture is heated for an hour at a temperature of 35°C and stirred.

The excess thionyl chloride and the by-products of the reaction are distilled under vacuum at a temperature not exceeding 50°C. To the obtained monoethyl o-phthalate chloride is added methylene chloride as a solvent and ferrocene, with stirring and passing an inert gas.

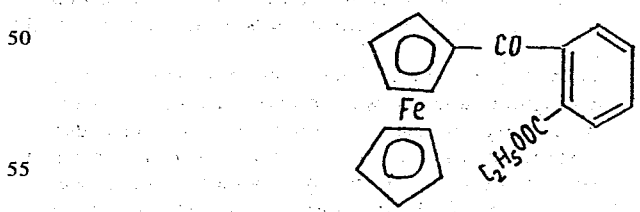

Gradually there is added to this mixture a suspension of aluminum chloride in dry methylene chloride or in a higher ether, or example, di-n-dibutyl ether, and the reaction mixture is heated at a temperature of 40°–45°C for 4–5 hours with stirring. The reaction mass is then cooled to 10°–15°C, and cool water acidified with hydrochloric acid is added thereto. Thereupon, the organic layer is separated and flushed with water, and the solvent is distilled off. Sodium hydroxide is added to the remaining ester of o-carboxybenzoyl ferrocene, and the mixture is heated at a temperature of 95°–98°C.

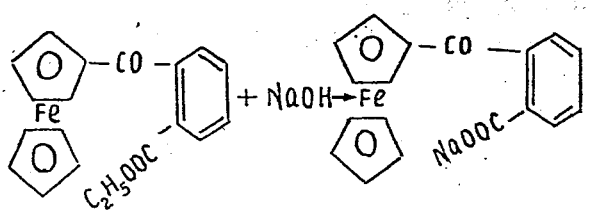

The obtained sodium salt of o-carboxybenzoyl ferrocene is filtered at a temperature of 80°C for separating tarry products. The filtrate is cooled down and the crystalline salt is separated and then purified by recrystallization from a minimum amount of water.

In order to obtain purer end products, said filtrate can be cooled and then acidified with hydrochloric acid, and o-carboxybenzoyl ferrocene can be separated and then heated with sodium hydroxide to prepare the end product. The process of the invention helps to simplify the technology of preparation owing to the use of ethyl alcohol as the lower aliphatic alcohol. In this case, liquid monoethyl o-phthalate is obtained following the removal of excess solvent, which makes it possible at the synthesis stage to carry out operations, such as preparing liquid monoester of phthalic acid, preparing the monoester chloride of phthalic acid and acylation to carry out the reaction, in a single apparatus without stage-to-stage separation of the intermediate products. An advantage of the method of the invention over the known one is the replacement of toxic methyl alcohol with non-toxic ethyl alcohol.

In addition, instead of carbon disulfide and absolute ether as a solvent (as is the case in the known process), in the proposed process use is made of readily available and non-flammable methylene chloride.

The process according to the present invention helps to prepare a high-quality end product suitable for medicinal purposes.

For a better understanding of the invention, presented hereinbelow are the following examples of carrying out the proposed process for preparing the sodium salt of o-carboxybenzoyl ferrocene, according to the invention.

EXAMPLE 1

In an enameled apparatus equipped with a stirrer, a jacket and a reflux condenser 3.5 kg of phthalic anhydride and 1.6 kg of absolute ethyl alcohol are charged through a connecting pipe. The reaction mass is heated at a temperature of 80°C until complete dissolution of the phthalic anhydride, after which the heating is continued for 30 minutes more. The excess alcohol is distilled in vacuum at a temperature not exceeding 50°C. Following the distillation of alcohol, the residue is cooled to a temperature of 20°C, 5 kg of thionyl chloride is gradually added to it and heated with stirring for one hour at a temperature of 35°C. Exhaust gases (via the reflux condenser are trapped in an absorbing system filled with alkaline solution. Then, the excess thionyl chloride is distilled in vacuum, and to the residue cooled down to a temperature of 20°C. 20 liters of dried methylene chloride and 4.3 kg of ferrocene are added with stirring and passing nitrogen therethrough. A suspension of 3.3 kg of anhydrous aluminum chloride in 40 liters of dried methylene chloride is added to the solution over a period of 35 minutes.

The reaction mass is heated for 4–5 hours at temperature of 40°C, and then cooled down to 2°–3°C.

To decompose the aluminum complex, acidified water (0.6 l hydrochloric acid to 10 l water) is added into the apparatus, the temperature during the course of addition being kept below 15°C. Then, 24 liters of water are added via the connecting pipe and stirred for 20–30 minutes. The aqueous layer is separated, and from the organic layer flushed with water to remove traces of hydrochloric acid, the sovent is distilled under vacuum (at a temperature not exceeding 40°C). To the residue 30 liters of water are added and 1.5 kg of sodium hydroxide is carefully charged with stirring, and then the mixture is heated at a temperature of 90°C until a sample taken therefrom is fully watersoluble. Thereupon, the hot reaction mass (80°–85°C) is filtered in a Nutsch filter to remove tar and to the filtrate, a solution of sodium salt of o-carboxybenzoyl ferrocene cooled down to 10°C is added diluted hydrochloric acid (1:1). The precipitated free o-carboxybenzoyl ferrocene acid is filtered in a Nutsch filter, flushed with cold water (10 to 15 l ) and thoroughly squeezed out. The paste with a moisture content of 30 per cent by weight weighs 7.5 kg, and the dry acid — 5.3 kg (69 per cent by weight of the theoretical, on the basis of ferrocene taken); m.p. 183°–184°C with decomposition. The paste for preparing the sodium salt is transferred to the apparatus containing the solution of 0.85 kg sodium hydroxide in 7.5 l of water heated to 50°–60°C, and the contents of the apparatus is heated with stirring to a temperature of 85°–90°C until complete dissolutin of the paste. The hot solution is transferred to a crystallizer where it is cooled to 5°–10°C. The precipitated salt is filtered off, squeezed out, flushed with ice-cold water in a Nutsch filter and squeezed out again.

The technical salt thus obtained is crystallized from 9 liters of distilled water. The yield of re-crystallized dry salt is 4.3 kg. Separated additionally from the mother liquors by adding hydrochloric acid is 0.55 kg o-carboxybenzoyl ferrocene recycled to obtain the sodium salt (0.5 kg). The total yield of the salt is 4.8 kg (49.8 per cent by weight of the theoretical, on the basis of ferrocene taken and assuming the sodium salt obtained to contain four molecules of water of crystallization.

EXAMPLE 2

The process is carried out analogously with Example 1 using as a catalyst a suspension of anhydrous aluminum chloride in n-dibutyl ether. The yield of the end product is 45 per cent by weight of the theoretical, on the basis of ferrocene taken and assuming the sodium salt obtained to contain four molecules of crystallization water.

What we claim is:

1. A process for preparing the sodium salt of o-carboxybenzoylferrocene which comprises reacting phthalic anhydride with ethyl alcohol under reflux to form monoethyl o-phthalate, reacting the monoethyl o-phthalate with thionyl chloride to form monoethyl o-phthaloyl monochloride, reacting the monochloride with the ferrocene in the presence of a catalyst which is a suspension of aluminum chloride in a solvent selected from the group consisting of methylene chloride and di-n-butyl ether to form the monoethyl ester of o-carboxybenzoylferrocene, reacting said ester with sodium hydroxide to form the sodium salt of o-carboxybenzoylferrocene and isolating said salt.

2. The process of claim 1 wherein said in a solvent is methylene chloride and.

3. The process of claim 1 wherein said solvent is di-n-butyl ether.

* * * * *